(12) United States Patent
Giliberti

(10) Patent No.: US 9,028,113 B1
(45) Date of Patent: May 12, 2015

(54) HANGING LAMP ASSEMBLY

(71) Applicant: Sean M. Giliberti, Wexford, PA (US)

(72) Inventor: Sean M. Giliberti, Wexford, PA (US)

( * ) Notice: Subject to any disclaimer, the term of this patent is extended or adjusted under 35 U.S.C. 154(b) by 0 days.

(21) Appl. No.: 13/937,439

(22) Filed: Jul. 9, 2013

(51) Int. Cl.
*F21V 5/00* (2006.01)
*F21V 9/12* (2006.01)
*F21V 33/00* (2006.01)
*F21S 10/00* (2006.01)

(52) U.S. Cl.
CPC ........... *F21V 33/0028* (2013.01); *F21S 10/002* (2013.01); *Y10S 362/806* (2013.01)

(58) Field of Classification Search
CPC ... A63H 33/3022; A63H 23/10; A63B 37/08; A63B 43/004; A63B 43/06; A63B 2037/082; A63B 2037/085; F21S 10/002
USPC .............. 362/96, 101, 230, 249.16, 318, 806; 446/219, 227, 485, 267; 428/11
See application file for complete search history.

(56) References Cited

U.S. PATENT DOCUMENTS

| | | | |
|---|---|---|---|
| 1,483,716 A | 2/1924 | Choinski | |
| 3,531,635 A * | 9/1970 | Hancock | 362/101 |
| 4,190,312 A * | 2/1980 | Bailey | 40/431 |
| 4,208,848 A | 6/1980 | Kohl | |
| 4,582,498 A * | 4/1986 | Tamada | 446/267 |
| 5,236,383 A * | 8/1993 | Connelly | 446/219 |
| 5,430,629 A | 7/1995 | Belliveau et al. | |
| 5,803,580 A | 9/1998 | Tseng | |
| 6,165,041 A * | 12/2000 | Lin | 446/267 |
| 6,206,536 B1 * | 3/2001 | Lin | 362/101 |
| 6,334,270 B1 * | 1/2002 | Ko | 40/406 |
| 6,415,534 B1 * | 7/2002 | Liao | 40/407 |
| 6,604,835 B2 | 8/2003 | Zale | |
| D480,497 S | 10/2003 | Lau Ting Yup | |
| 6,938,833 B2 * | 9/2005 | Chen | 239/44 |
| D639,494 S | 6/2011 | Schrimmer | |
| 2002/0089846 A1 * | 7/2002 | Shu | 362/118 |
| 2002/0149926 A1 * | 10/2002 | Tee et al. | 362/101 |
| 2004/0095748 A1 | 5/2004 | Lin | |
| 2007/0206375 A1 * | 9/2007 | Piepgras et al. | 362/147 |
| 2008/0089055 A1 * | 4/2008 | Ichikawa | 362/101 |
| 2008/0239705 A1 * | 10/2008 | Lin et al. | 362/101 |
| 2009/0117817 A1 * | 5/2009 | Lin | 446/267 |
| 2009/0312127 A1 * | 12/2009 | Kessler | 473/570 |
| 2010/0184541 A1 * | 7/2010 | Kessler | 473/570 |
| 2010/0327766 A1 * | 12/2010 | Recker et al. | 315/291 |

FOREIGN PATENT DOCUMENTS

EP          0323193 A2 *   7/1989

\* cited by examiner

*Primary Examiner* — Peggy Neils
*Assistant Examiner* — James Endo

(57) ABSTRACT

A hanging lamp assembly provides visual stimulation and relaxation. The assembly includes a container having a transparent perimeter wall defining an interior space. A first fluid and a second fluid are positioned in the interior space defining a liquid mass. The second fluid has a density different than a density of the first fluid wherein the first fluid and the second fluid are layered within the interior space defining a fluid interface between the first liquid and the second liquid. The first fluid is a non-clear color and the second fluid is a different color than the first fluid. A plurality of items is positioned in the interior space such that the items are suspended in the liquid mass. A light source is coupled to the container directing light towards the liquid mass. A hanger is coupled to the container such that the container swings freely from a supporting structure.

19 Claims, 3 Drawing Sheets

HANGING LAMP ASSEMBLY

BACKGROUND OF THE DISCLOSURE

Field of the Disclosure

The disclosure relates to lamp devices and more particularly pertains to a new lamp device for providing visual stimulation and relaxation during swinging or spinning movement of the lamp.

SUMMARY OF THE DISCLOSURE

An embodiment of the disclosure meets the needs presented above by generally comprising a container having a transparent perimeter wall defining an interior space. A first fluid and a second fluid are positioned in the interior space defining a liquid mass. The second fluid has a density different than a density of the first fluid wherein the first fluid and the second fluid are layered within the interior space defining a fluid interface between the first liquid and the second liquid. The first fluid is a non-clear color and the second fluid is a different color than the first fluid. A plurality of items is positioned in the interior space such that the items are suspended in the liquid mass. A light source is coupled to the container directing light towards the liquid mass. A hanger is coupled to the container such that the container swings freely from a supporting structure.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
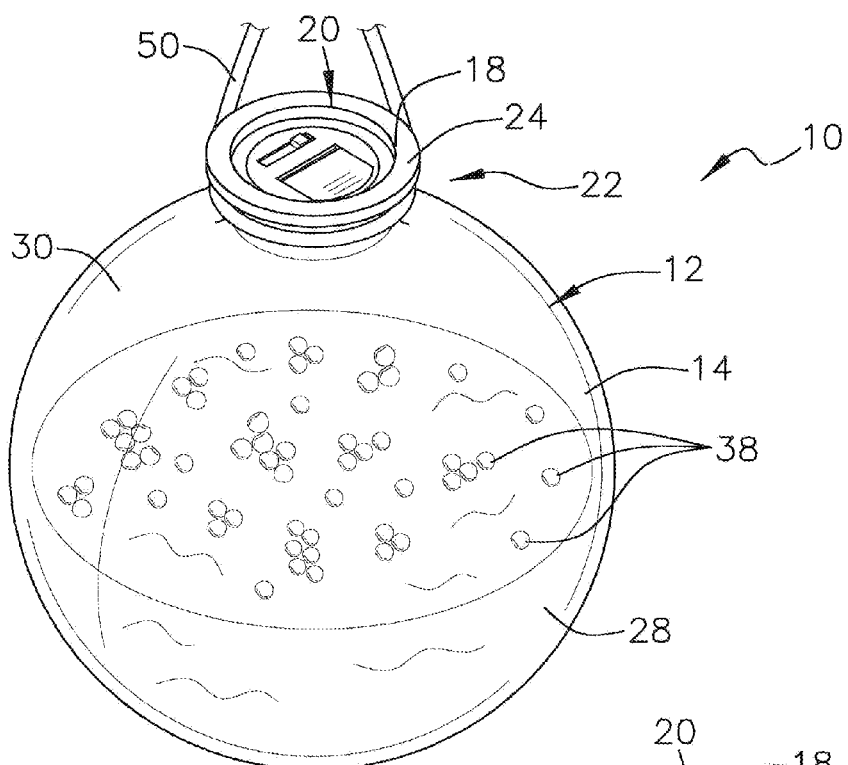
FIG. 1 is a top front side perspective view of a hanging lamp assembly according to an embodiment of the disclosure.
Figure 2:
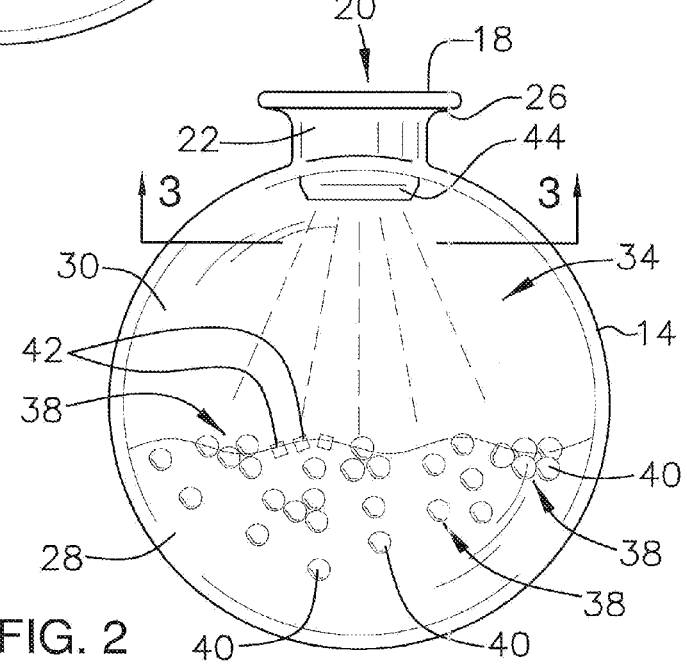
FIG. 2 is a front view of an embodiment of the disclosure.
Figure 3:
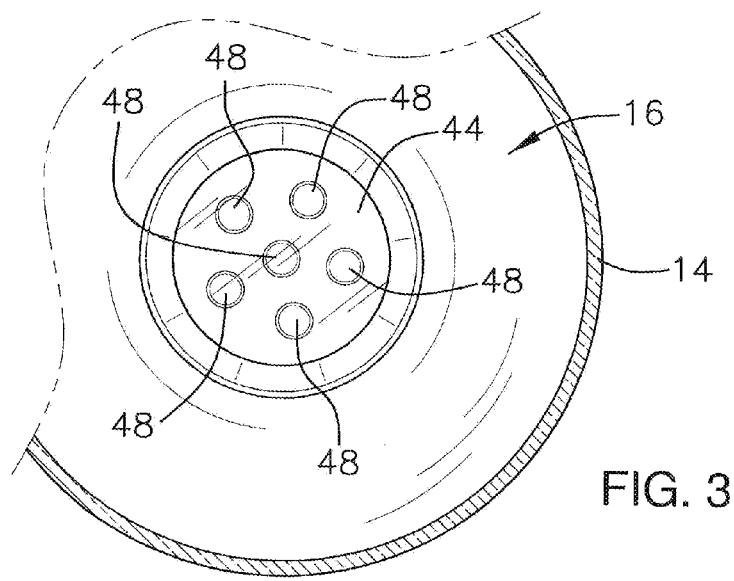
FIG. 3 is a cross-sectional view of an embodiment of the disclosure taken along line 3-3 of FIG. 2.
Figure 4:
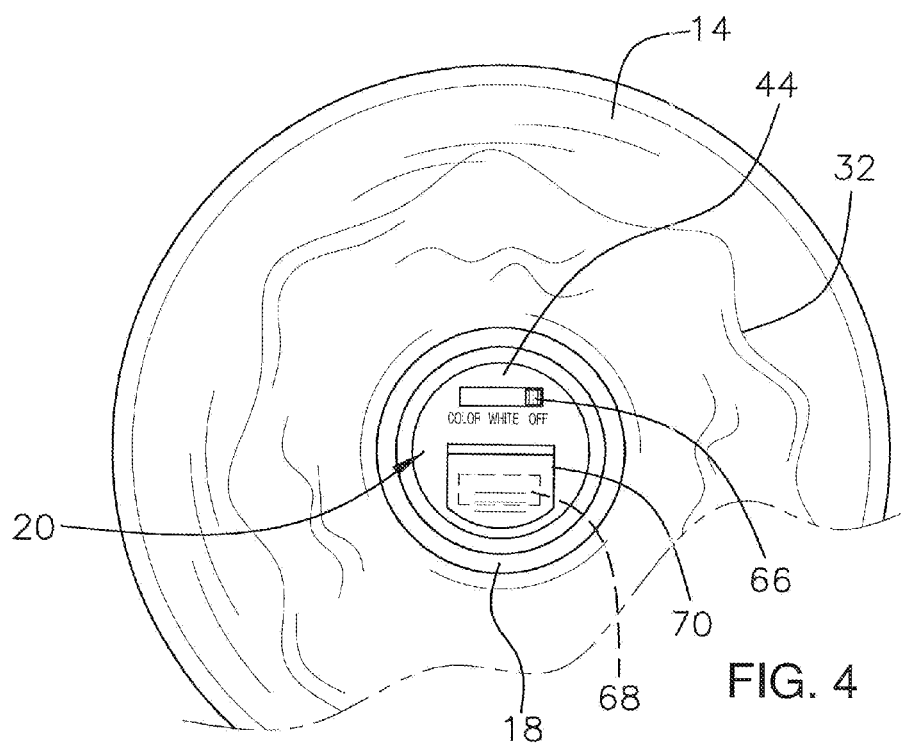
FIG. 4 is a partial top view of an embodiment of the disclosure.
Figure 5:
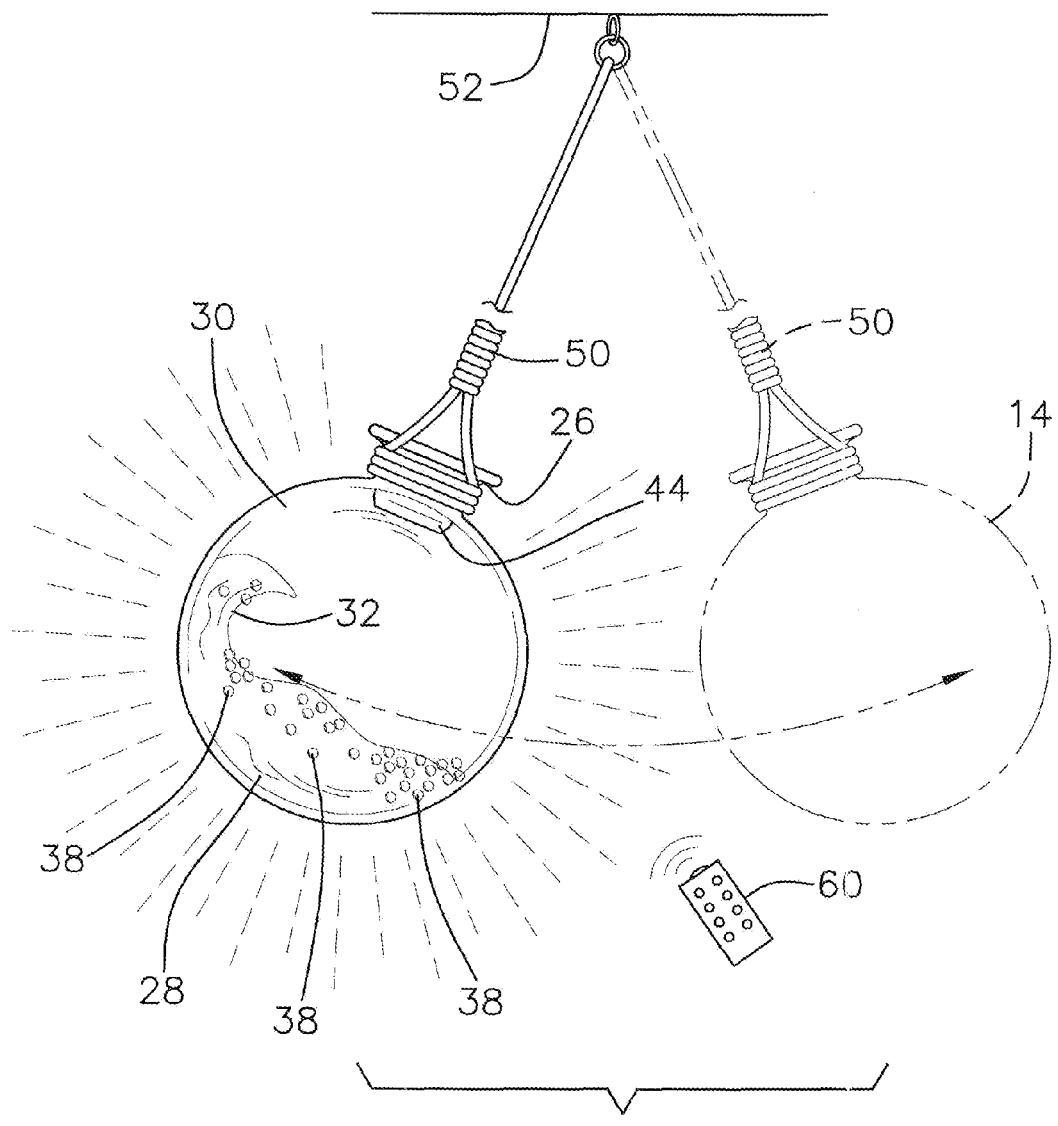
FIG. 5 is a front view of an embodiment of the disclosure in use.

With reference now to the drawings, and in particular to FIGS. 1 through 5 thereof, a new lamp device embodying the principles and concepts of an embodiment of the disclosure and generally designated by the reference numeral 10 will be described.

As best illustrated in FIGS. 1 through 5, the hanging lamp assembly 10 generally comprises a container 12 having a transparent perimeter wall 14 defining an interior space 16. A top edge 18 of the perimeter wall 14 defines an opening 20 into the interior space 16. The container 12 may be substantially spherical having a neck portion 22 adjacent to the opening 20 into the interior space 16. The neck portion 22 may have a top section 24 flared outwardly providing a lip 26 extending around the opening 20.

A first fluid 28 is positioned in the interior space 16. The first fluid 28 may be a non-clear color. The first fluid 28 may be water colored by a dye such as food coloring or the like. A second fluid 30 is positioned in the interior space 16. The second fluid 30 may be mineral oil or the like a density different than a density of the first fluid 28. Thus, the first fluid 28 and the second fluid 30 are layered within the interior space 16 when at rest defining a fluid interface 32 between the first liquid 28 and the second liquid 30. The second fluid 30 is a different color than the first fluid 28. The second fluid 30 may also be clear. The first liquid 28 and the second liquid 30 define a liquid mass 34 within the interior space 16.

A plurality of items 38 is positioned in the interior space 16 such that the items 38 are suspended in the liquid mass 34. Each item 38 may be a cotton ball 40, tin foil 42 or another such item having a density between the density of the first fluid 28 and the density of the second fluid 30. Thus, each item 38 is positioned in the fluid interface 32 when the container 12 is at rest. Alternatively, the same effect may be achieved by shaping of an item 38 to allow surface tension at the fluid interface 32 to suspend the item 38 within the liquid mass 34.

A light source 44 is coupled to the container 12. The light source 44 may be coupled to and seal the opening 20 into the interior space 16. The light source 44 is directs light towards the liquid mass 34. The first liquid 28 and the second liquid 30 may have translucent qualities to disperse illumination from the light source 44 resulting in a glowing appearance within the interior space 16 of the container 12. The light source 44 may comprise a plurality of light emitting diodes 48 in a plurality of colors provided by either separately colored lights or individual lights capable of changing colors. The light source 44 may be programmable wherein the light source 44 changes the color of light in a series of single colors from the plurality of colors. Combinations of colors may also be provided randomly or in various patterns. Each color of light provided may be selectable such that a single selectable color of light is provided by the light source 44 at one time allowing a user to choose and view a favorite color. This may be achieved using a switch 66 on the light source 44. A battery 68 is coupled to the light source 44 within a compartment 70. A remote control 60 may be communicatively coupled to the light source 44 wherein the light source 44 is controllable by manipulation of the remote control 60 permitting control of the light colors while the container 12 swings freely creating agitation within the interior space 16.

A hanger 50 is coupled to the container 12. The hanger 50 extends from the container 12 and is configured for hanging the container 12 such that the container 12 swings freely from a supporting structure 52. The hanger 50 may be coupled to the neck portion 22 of the perimeter wall 14 such that the container 12 is supported on the hanger 50 by the lip 26. Thus, the hanger 50 does not extend downwardly to obscure view through the perimeter wall 14. Alternatively, the hanger 50 may comprise a sling shaped to suspend and support the container 12. The hanger 50 may incorporate structures such as swivels or a lack of swivels to effect the nature of movement as the container 12 swings and twists when acted upon by a user.

In use, the light source 44 is activated to illuminate the liquid mass 34 in the interior space 16. The container 12 is urged to move in a swing motion, spinning motion, or combination of motions such that the liquid mass 34 is agitated within the container 12. Agitation of the liquid mass 34 produces agitation and variation in the appearance of the fluid interface 32. The items 38 present in the interior space 16 further enhance the changes in the appearance of the fluid interface 32 providing greater levels of detail and effect on the light directed into the liquid mass 34. Thus, the assembly 10 may provide visual stimulation and relaxation to a person viewing the liquid mass 34 in the interior space 16 of the container 12 as the container 12 moves.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A hanging lamp assembly comprising:
   a container having a transparent perimeter wall defining an interior space, a top edge of said perimeter wall defining an opening into said interior space;
   a first fluid being positioned in said interior space, said first fluid being a non-clear color;
   a second fluid being positioned in said interior space, said second fluid having a density different than a density of said first fluid wherein said first fluid and said second fluid are layered within said interior space defining a fluid interface between said first fluid and said second fluid, said second fluid being a different color than said first fluid, said first fluid and said second fluid defining a liquid mass within said interior space;
   a plurality of items positioned in said interior space such that said items are suspended in said liquid mass, each of said items comprising a unitary structure;
   a light source coupled to said container, said light source directing light towards said liquid mass; and
   a hanger coupled to said container, said hanger extending from said container, said hanger being configured for hanging said container such that said container swings freely from a supporting structure.

2. The assembly of claim 1, further comprising said perimeter wall having a neck portion adjacent to said opening into said interior space, said hanger being coupled to said neck portion of said perimeter wall.

3. The assembly of claim 1, further comprising said light source comprising a plurality of light emitting diodes.

4. The assembly of claim 1, further comprising said light source being coupled to and sealing said opening into said interior space.

5. The assembly of claim 1, further comprising said light source providing light in a plurality of colors.

6. The assembly of claim 5, further comprising each color of light provided being selectable such that a single selectable color of light is provided by said light source at one time.

7. The assembly of claim 5, further comprising said light source being programmable wherein said light source changes said color of light in a series of said plurality of colors.

8. The assembly of claim 1, further comprising a remote control communicatively coupled to said light source wherein said light source is controllable by manipulation of said remote control.

9. The assembly of claim 1, further comprising each said item being an item chosen from the group of items consisting of cotton balls and tin foil.

10. The assembly of claim 1, further comprising said container being substantially spherical.

11. The assembly of claim 1, further comprising each said item having a density between said density of said first fluid and said density of said second fluid wherein each said item is positioned in said fluid interface when said container is at rest.

12. A hanging lamp assembly comprising:
    a container having a transparent perimeter wall defining an interior space, a top edge of said perimeter wall defining an opening into said interior space, said container being substantially spherical, said perimeter wall having a neck portion adjacent to said opening into said interior space;
    a first fluid being positioned in said interior space, said first fluid being a non-clear color;
    a second fluid being positioned in said interior space, said second fluid having a density different than a density of said first fluid wherein said first fluid and said second fluid are layered within said interior space defining a fluid interface between said first fluid and said second fluid, said second fluid being a different color than said first fluid, said first fluid and said second fluid defining a liquid mass within said interior space;
    a plurality of items positioned in said interior space such that said items are suspended in said liquid mass, each said item being an item chosen from the group of items consisting of cotton balls and tin foil, each said item having a density between said density of said first fluid and said density of said second fluid wherein each said item is positioned in said fluid interface when said container is at rest;
    a light source coupled to said container, said light source being coupled to and sealing said opening into said interior space, said light source directing light towards said liquid mass, said light source comprising a plurality of light emitting diodes, said light source providing light in a plurality of colors, said light source being programmable wherein said light source changes said color of light in a series of said plurality of colors, each color of light provided being selectable such that a single selectable color of light is provided by said light source at one time;
    a hanger coupled to said container, said hanger extending from said container, said hanger being configured for hanging said container such that said container swings freely from a supporting structure, said hanger being coupled to said neck portion of said perimeter wall; and
    a remote control communicatively coupled to said light source wherein said light source is controllable by manipulation of said remote control.

13. A hanging lamp assembly comprising:
    a container having a transparent perimeter wall defining an interior space, a top edge of said perimeter wall defining an opening into said interior space;
    a first fluid being positioned in said interior space, said first fluid being a non-clear color;

a second fluid being positioned in said interior space, said second fluid having a density different than a density of said first fluid wherein said first fluid and said second fluid are layered within said interior space defining a fluid interface between said first fluid and said second fluid, said second fluid being a different color than said first fluid, said first fluid and said second fluid defining a liquid mass within said interior space;

a plurality of items positioned in said interior space such that said items are suspended in said liquid mass;

a light source coupled to said container, said light source directing light towards said liquid mass;

a hanger coupled to said container, said hanger extending from said container, said hanger being configured for hanging said container such that said container swings freely from a supporting structure; and a remote control communicatively coupled to said light source wherein said light source is controllable by manipulation of said remote control.

14. The assembly of claim 13, further comprising said light source providing light in a plurality of colors.

15. The assembly of claim 14, further comprising each color of light provided being selectable such that a single selectable color of light is provided by said light source at one time.

16. The assembly of claim 14, further comprising said light source being programmable wherein said light source changes said color of light in a series of said plurality of colors.

17. The assembly of claim 13, further comprising each said item being an item chosen from the group of items consisting of cotton balls and tin foil.

18. The assembly of claim 13, further comprising said container being substantially spherical.

19. The assembly of claim 13, further comprising each said item having a density between said density of said first fluid and said density of said second fluid wherein each said item is positioned in said fluid interface when said container is at rest.

* * * * *